United States Patent
Cobbinah et al.

(10) Patent No.: US 8,063,375 B2
(45) Date of Patent: Nov. 22, 2011

(54) SENSIBLE MOTION DETECTOR

(75) Inventors: Kofi B. Cobbinah, Houston, TX (US); Marzyeh Ghassemi, Hillsboro, OR (US)

(73) Assignee: Intel-GE Care Innovations LLC, Roseville, CA (US)

( * ) Notice: Subject to any disclaimer, the term of this patent is extended or adjusted under 35 U.S.C. 154(b) by 231 days.

(21) Appl. No.: 11/766,878

(22) Filed: Jun. 22, 2007

(65) Prior Publication Data

US 2008/0316025 A1    Dec. 25, 2008

(51) Int. Cl.
    *G08B 13/18*    (2006.01)
(52) U.S. Cl. ............ 250/353; 250/347; 250/338.3
(58) Field of Classification Search ............... 250/353, 250/347, 338.3
    See application file for complete search history.

(56) References Cited

U.S. PATENT DOCUMENTS

| | | | |
|---|---|---|---|
| 3,396,397 A * | 8/1968 | Kott ............................. 343/754 |
| 3,725,888 A * | 4/1973 | Solomon ....................... 340/522 |
| 3,792,470 A * | 2/1974 | Donovan et al. ............. 340/509 |
| 4,660,024 A | 4/1987 | McMaster |
| 4,719,485 A * | 1/1988 | Shikaumi ........................ 396/78 |
| 4,833,450 A * | 5/1989 | Buccola et al. ............. 340/506 |
| 4,947,152 A | 8/1990 | Hodges |
| 5,331,308 A * | 7/1994 | Buccola et al. ............. 340/522 |
| 5,473,311 A * | 12/1995 | Hoseit ........................ 340/573.1 |
| 5,670,943 A | 9/1997 | DiPoala et al. |
| 5,818,337 A * | 10/1998 | Erismann ..................... 340/567 |
| 5,936,666 A * | 8/1999 | Davis ........................... 348/143 |
| 6,166,644 A | 12/2000 | Stroda |
| 6,211,522 B1 * | 4/2001 | Kotlicki et al. ............. 250/353 |
| 6,215,399 B1 * | 4/2001 | Shpater ........................ 340/567 |
| 6,239,736 B1 | 5/2001 | McDonald et al. |
| 6,323,488 B1 * | 11/2001 | McCavit et al. ............. 250/347 |
| 6,351,234 B1 | 2/2002 | Choy |
| 6,380,882 B1 * | 4/2002 | Hegnauer ....................... 342/28 |
| 6,583,720 B1 | 6/2003 | Quigley |
| 7,026,601 B2 * | 4/2006 | Tsuji ............................. 250/221 |
| 7,071,820 B2 | 7/2006 | Callaway |
| 7,079,028 B2 * | 7/2006 | Herrmann et al. ........... 340/541 |
| 7,375,630 B2 * | 5/2008 | Babich et al. ................ 340/567 |
| 2003/0185419 A1 * | 10/2003 | Sumitomo .................... 382/103 |
| 2004/0032326 A1 * | 2/2004 | Nakamura et al. ........... 340/567 |
| 2004/0135688 A1 * | 7/2004 | Zhevelev et al. ............ 340/565 |
| 2004/0145457 A1 * | 7/2004 | Schofield et al. ......... 340/425.5 |
| 2004/0160324 A1 | 8/2004 | Stilp |

(Continued)

FOREIGN PATENT DOCUMENTS

EP    1566781 A1    8/2005

(Continued)

OTHER PUBLICATIONS

Cirino, Giuseppe A. et al., "Fresnel Lens Array With Spatial Filtering for Passive Infrared Motion Sensor Applications", XXIX ENFMC, Annuals of Optics, 2006, 4 pages.

(Continued)

*Primary Examiner* — David Porta
*Assistant Examiner* — Djura Malevic
(74) *Attorney, Agent, or Firm* — Pillsbury Winthrop Shaw Pittman LLP

(57) ABSTRACT

According to some embodiments, an apparatus having a first sensor having a first adjustable lens and a second sensor having a second adjustable lens is disclosed. A controller is coupled to the first sensor and the second sensor. The controller is to cause the first sensor and the second sensor to operate independently in a first mode and is to cause the first motion sensor and the second motion sensor to operate interdependently in a second mode.

24 Claims, 5 Drawing Sheets

U.S. PATENT DOCUMENTS

| | | | |
|---|---|---|---|
| 2004/0179100 A1* | 9/2004 | Ueyama | 348/152 |
| 2005/0151647 A1 | 7/2005 | Alkelai et al. | |
| 2006/0186326 A1* | 8/2006 | Ito | 250/234 |
| 2007/0008411 A1* | 1/2007 | Shibata et al. | 348/152 |
| 2007/0023662 A1* | 2/2007 | Brady et al. | 250/338.3 |
| 2007/0145277 A1* | 6/2007 | Zhevelev et al. | 250/353 |
| 2007/0152156 A1* | 7/2007 | Zhevelev et al. | 250/339.14 |
| 2008/0043106 A1* | 2/2008 | Hassapis et al. | 348/153 |
| 2008/0165001 A1* | 7/2008 | Drake et al. | 340/550 |
| 2008/0272281 A1* | 11/2008 | Stromberg et al. | 250/216 |

FOREIGN PATENT DOCUMENTS

| | | |
|---|---|---|
| FR | 2842306 A1 | 1/2004 |
| JP | 56112653 A | 9/1981 |
| JP | 3199929 A | 4/1995 |
| KR | 1020020084566 A | 11/2002 |
| WO | WO 2006/135962 A1 | 12/2006 |

OTHER PUBLICATIONS

Porter, Jess, et al., "Mechanisms of Scent-Tracking in Humans", Nature Neuroscience, vol. 10, No. 1, Jan. 2007, 3 pages.

Supplementary European Search Report corresponding to European Application No. 08795897, dated Sep. 17, 2010.

Chinese Office Action with English translation corresponding to Chinese patent application No. 200880021509.7, dated Aug. 24, 2010.

* cited by examiner

SENSIBLE MOTION DETECTOR

BACKGROUND

Many motion sensors available today are suitable primarily for security purposes. For example, when a motion sensor detects motion, an alarm may sound, or a light may turn on. Motion sensors are typically not used as a tool to measure or infer a person's daily activity.

A motion sensor with the ability to detect a patient and monitor the patient's movements, the frequency of those movements, and the habits of those movements could assist caregivers or physicians responsible for the patient.

BRIEF DESCRIPTION OF THE DRAWINGS

A better understanding of embodiments of the present invention can be obtained from the following detailed description in conjunction with the following drawings, in which.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure an understanding of this description.

References to "one embodiment," "an embodiment," "example embodiment," "various embodiments," etc., indicate that the embodiments) of the invention so described may include particular features, structures, or characteristics, but not every embodiment necessarily includes the particular features, structures, or characteristics. Further, some embodiments may have some, all, or none of the features described for other embodiments.

In the following description and claims, the terms "coupled" and "connected," along with their derivatives, may be used. It should be understood that these terms are not intended as synonyms for each other. Rather, in particular embodiments, "connected" is used to indicate that two or more elements are in direct physical or electrical contact with each other. "Coupled" is used to indicate that two or more elements co-operate or interact with each other, but they may or may not be in direct physical or electrical contact.

As used in the claims, unless otherwise specified the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

Various embodiments of the invention may be implemented in one or any combination of hardware, firmware, and software. Embodiments of the invention may also be implemented as instructions contained in or on a machine-readable medium, which may be read and executed by one or more processors to enable performance of the operations described herein. A machine-readable medium may include any mechanism for storing, transmitting, and/or receiving information in a form readable by a machine (e.g., a computer). For example, a machine-readable medium may include a storage medium, such as but not limited to read only memory (ROM); random access memory (RAM); magnetic disk storage media; optical storage media; a flash memory device, etc. A machine-readable medium may also include a propagated signal which has been modulated to encode the instructions, such as but not limited to electromagnetic, optical, or acoustical carrier wave signals.

The term "wireless" and its derivatives may be used to describe circuits, devices, systems, methods, techniques, communications channels, etc., that communicate data by using modulated electromagnetic radiation through a non-solid medium. The term does not imply that the associated devices do not contain any wires, although in some embodiments they might not.

Figure 1:
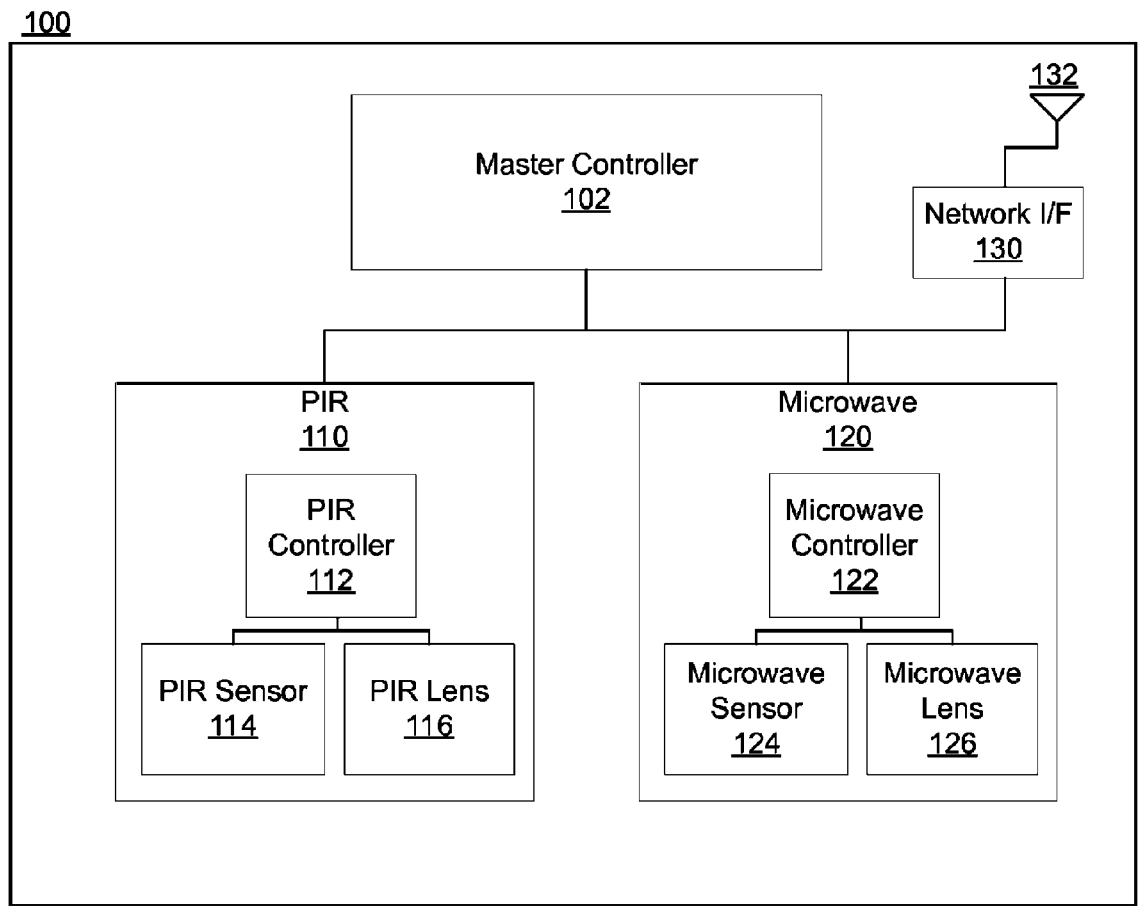
FIG. 1 is a block diagram of a wireless motion detection system according to some embodiments.

FIG. 1 is a block diagram of a wireless motion detection system 100 according to some embodiments. The wireless motion detection system uses two sensor technologies to sense motion, pyroelectric infrared (PIR) 110, and microwave 120.

A PIR sensor module 110 may include a PIR controller 112, a PIR sensor 114 and a PIR lens 116. The PIR lens 116 may in some embodiments be an adjustable lens that is capable of zooming in or out on a specific region or subject. The PIR controller 112 may control a zoom level of the PIR sensor 114 and the PIR lens 116, in order to zoom in or out on a detected subject.

A microwave sensor module 120 may include a microwave controller 122, a microwave sensor 124 and a microwave lens 126. The microwave lens 126 may in some embodiments be an adjustable lens that is capable of zooming in or out on a specific region or subject. The microwave controller 122 may control a zoom level of the microwave sensor 124 and the microwave lens 126, in order to zoom in or out on a detected subject.

The PIR lens 116 and the microwave lens 126 may in some embodiments be Fresnel lenses. Use of a Fresnel lens may permit the system to distinguish between a primary subject and a non-primary subject (a guest, co-habitants, etc.) by measuring the height of the sensed objects. In some embodiments, the detected image may be vertically enhanced by the master controller or by another processor so that a height distinction can be made between two adults of different heights and/or weights.

A master controller 102 may be coupled to the PIR controller, sensor, and lens, and to the microwave controller, sensor, and lens. The master controller may be, for example, a microprocessor. The master controller may receive data from the PIR sensor 114 and/or the microwave sensor 124, and based on the data received, may direct the PIR controller 112 and/or the microwave controller 122 to zoom in on a subject or area of motion by adjusting the position of one or more lenses and/or sensors. In some embodiments, the functionality of the PIR controller 112 and the microwave controller 122 may be integrated into the master controller 102.

In some embodiments, the master controller 102 may determine based upon data received from one or both sensors 114, 124 that one of the sensors is not suitable for detecting motion at a particular time. For example, while the subject is detected moving quickly around the room, PIR technology may not be suitable for detecting the motion of the subject. Similarly, while the subject is still or moving very slowly, microwave technology may not be suitable for detecting the motion of the subject. If one sensor is not suitable for detecting the type of motion that is occurring, the sensors may operate independently of one another, and the master controller may choose to receive data from only one sensor while placing the other sensor in a low power or sleep mode. Additionally, if the subject is out of range of one sensor, that sensor may be placed in a low power mode while the other sensor is used to track the subject, sending data to the master controller for processing.

If both sensors are suitable for detecting the type of motion that is occurring, the sensors may operate interdependently, and the master controller may receive data from both the PIR and microwave sensor simultaneously. In an interdependent mode, the master controller may localize the motion sensed by comparing simultaneous inputs across the two sensor technologies by converting the difference in motion timing and intensity into spatial coordinates. These spatial coordinates may be used to direct the lenses to zoom in or out on the area of motion.

The master controller 102 may be coupled to a network interface 130. The network interface 130 may be a wired or wireless interface. In some embodiments, the network interface is a wireless interface including an antenna 132. In some embodiments, the antenna 132 may be a dipole antenna. The network interface 130 may enable wireless communication between the motion detection system and other systems or devices. For example, the system may transmit data related to the movements of a primary subject to a computer or handheld device belonging to a remote caregiver or to a physician. This information may then be used by the remote caregiver or physician, for example, to ensure that the subject is functioning normally and/or is performing routine daily tasks.

Figure 2:
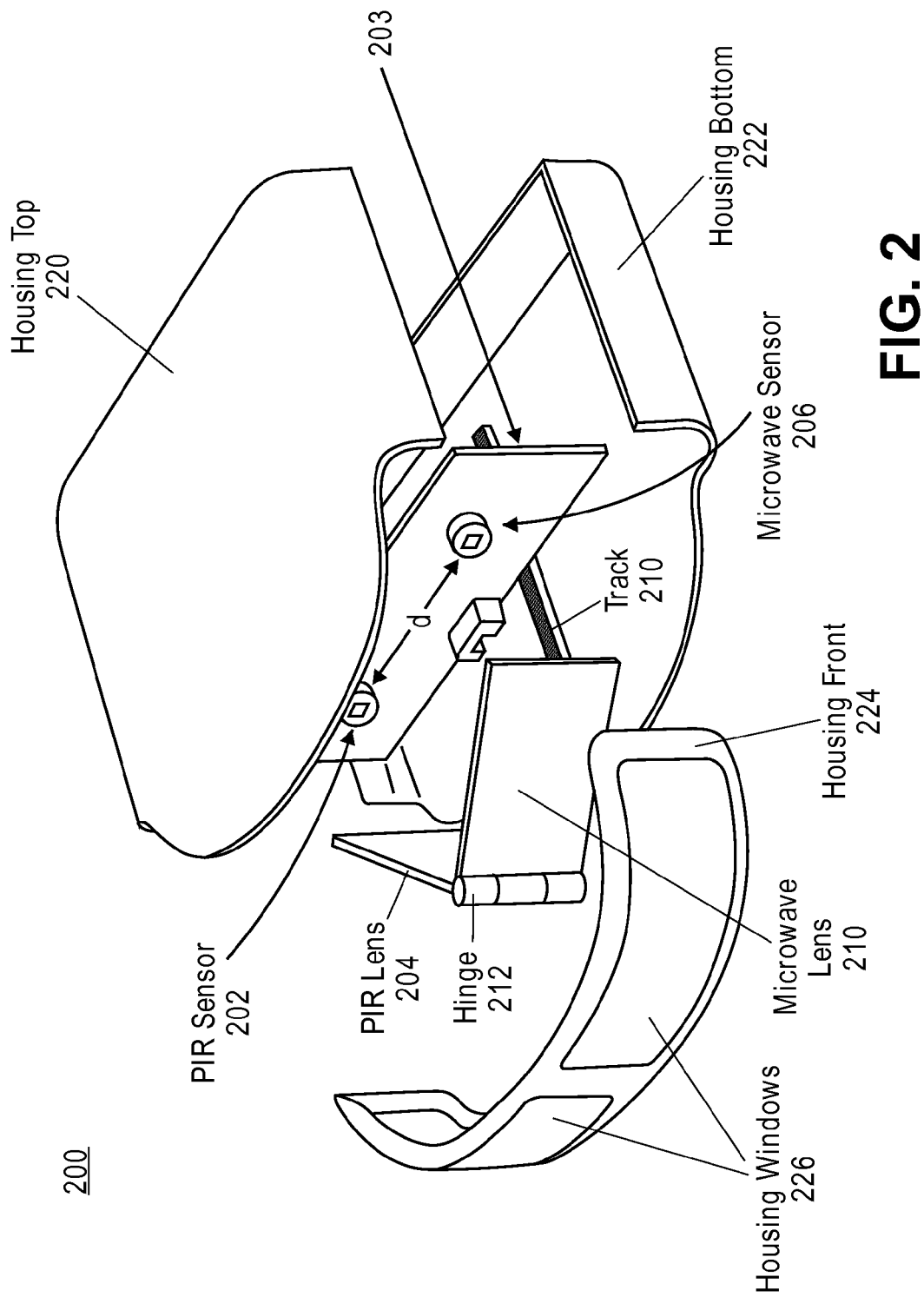
FIG. 2 is a diagram illustrating a motion sensing device according to some embodiments.

FIG. 2 is a diagram illustrating a motion sensing device 200 according to some embodiments. The motion sensing device 200 is enclosed in a housing that includes a housing top 220, a housing bottom 222, and a housing front 224. The housing front 224 may include housing windows 226 to allow each of two motion sensors to sense motion outside of the housing.

As described above with respect to FIG. 1, the motion sensing device 200 includes two sensors, a PIR sensor 202 and a microwave sensor 206. The PIR sensor 202 and the microwave sensor 204 may be mounted on a vertical plate 203 within the housing, and may be separated by a distance, d. In some embodiments, the sensors may be separated by a distance, d, of approximately 3.5 cm, however it should be recognized that other separation distances may also be used. The separation distance may give the motion sensor technologies the ability to target motion that is outside of the others' range plane or field of view. Depending on the location of the subject and the subject's activity level, either a single motion sensor technology may be used to track the subject or dual motion sensor technology may be used to track the subject.

The motion sensing device 200 also includes two lenses, a PIR lens 204 associated with the PIR sensor 202, and a microwave lens 208 associated with the microwave sensor 206. In some embodiments the PIR lens 204 and the microwave lens 208 may be Fresnel lenses.

In some embodiments, the PIR lens 204 and the microwave lens 208 may be connected to one another at a hinged joint 212. The hinged joint 212 may be configured to control the angle and/or the position of the lenses 204, 208 with respect to each other and/or the sensors 202, 206.

In some embodiments, the hinged joint 212 may be configured to move along a rail or track 210, thus moving the PIR lens 204 and/or the microwave lens 208 closer to or away from the PIR sensor 202 and/or the microwave sensor 206, respectively. Similarly, the vertical plate 203 on which the sensors are mounted may be configured to move along the track 210 to move the sensors closer to or away from the lenses. By moving the lenses and/or the sensors along the track, the zoom level of the sensors may be changed, thus allowing the sensor to zoom in on an area of motion or a subject of interest. In some embodiments, the lenses may be capable of zooming independently of one another.

In some embodiments, the PIR lens 204 and the microwave lens 208 may not be connected at a hinged joint, but may still be capable of being moved toward or away from the sensors independently or interdependently to provide zoom capability.

It should be noted that while a single housing is illustrated to house both types of sensors and both lenses, in some embodiments each sensor and its corresponding lens may be in a separate housing and placed in a separate area of the room. In such embodiments, the sensors may communicate with each other and with a master controller via a wired or wireless interface.

Figure 3:
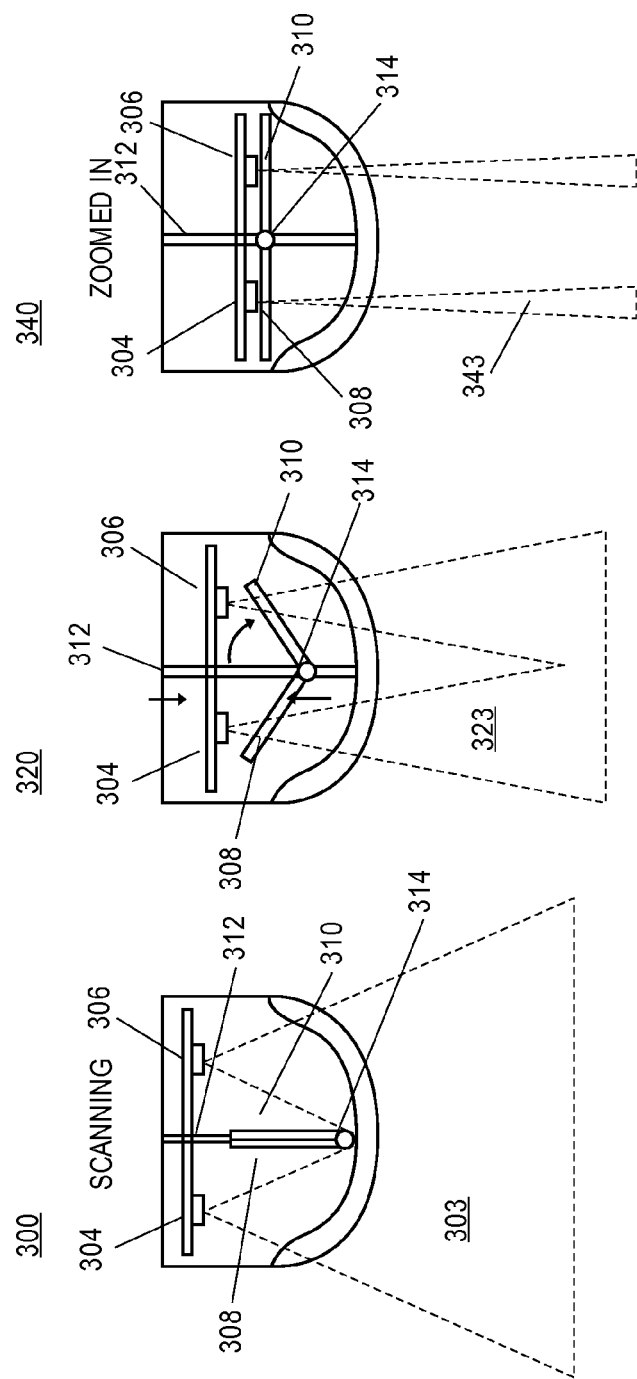
FIG. 3 is a diagram illustrating a top view of a motion sensing device according to some embodiments.

FIG. 3 is a diagram illustrating a top view of a motion sensing device according to some embodiments. Sensing device 300 is illustrated performing a scan of a room. During a scan, the device 300 may perform a scan of its field of view 303 with the PIR sensor 304 for a predetermined time period while the microwave sensor 306 is in a low power or sleep mode. After the predetermined period, the PIR sensor 304 may go into a low power or sleep mode while the microwave sensor 306 performs a scan of its field of view for the predetermined time period. During the scan period, one or both sensors may continuously monitor the room for movement and/or changes in temperature. The lenses 308, 310 may be retracted along the track 312 during the scan period because it is not necessary to zoom until a subject has been detected.

When motion is detected in the field of view 303 via movement or body temperature, the device 320 begins to zoom in on the detected subject. The sensors 304, 306 may move toward the lenses along the track 312, and/or the lenses 308, 310 may swing away from one another on a hinge 314 while the hinge moves toward the sensors along the track 312. The field of view 323 begins to narrow while zooming in on the subject.

In some embodiments, the device 340 may be zoomed in on a subject at a maximum focal length, leaving the field of view 343 narrow.

Figure 4:
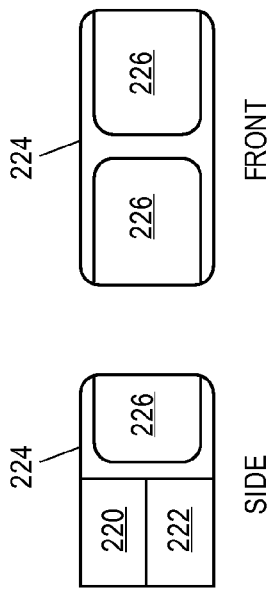
FIG. 4 is a diagram illustrating a side and front view of a motion sensing device according to some embodiments.

FIG. 4 is a diagram illustrating a side and front view of a motion sensing device housing according to some embodiments. As described above with respect to FIG. 2, the motion sensing device is enclosed in a housing that includes a housing top 220, a housing bottom 222, and a housing front 224. The housing front 224 may include housing windows 226 to allow each of two motion sensors to sense motion outside of the housing.

Figure 5:
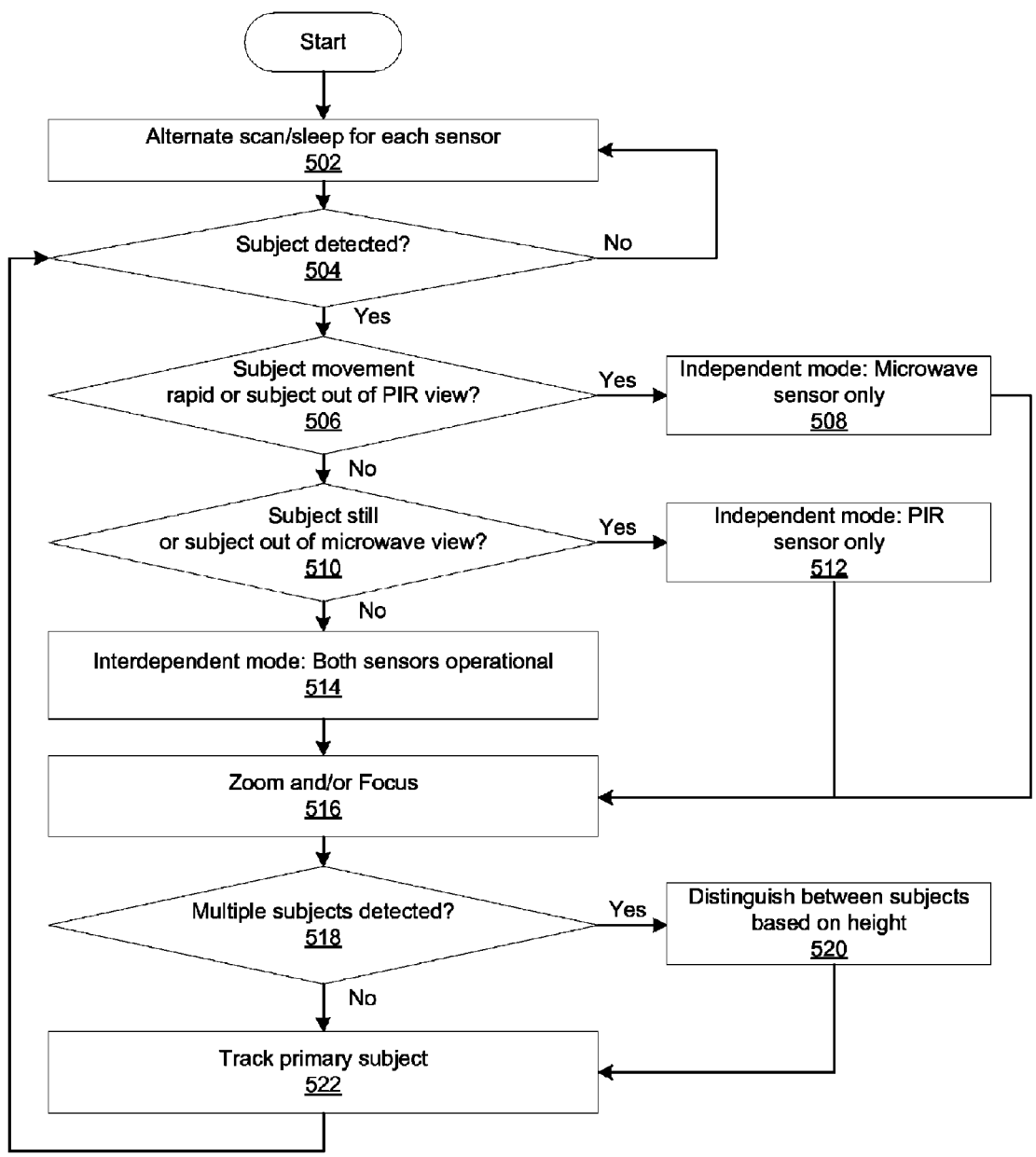
FIG. 5 is a flow diagram illustrating detection and tracking of a subject using a motion sensing device according to some embodiments.

FIG. 5 is a flow diagram illustrating detection and tracking of a subject using a motion sensing device having a PIR sensor and a microwave sensor according to some embodiments. At least one sensor may constantly monitor a room for movement and/or changes in human temperature. In some embodiments, one sensor is operable and scans for a predetermined time period while the second sensor is in a low power or sleep mode. In some embodiments, the predetermined time period may be approximately one minute. The sensors alternate operating in scan mode and in sleep mode 502, with one sensor scanning and the other sleeping until a subject is detected 504.

After a subject has been detected, a determination whether to use one or both sensors is made depending on the location and/or type of movement detected. If the subject movement is rapid, for example, too rapid to be accurately detected by a PIR sensor or if the subject is out of range of the PIR sensor, as shown in block 506, then the motion sensing device will operate in an independent mode with only the microwave sensor operational 508. If the subject movement is slow, for example, too slow to be accurately detected by a microwave sensor or if the subject is out of range of the microwave sensor, as shown in block 510, then the motion sensing device will operate in an independent mode with only the PIR sensor operational 512. If the subject movement is in a range where it can be accurately detected by the PIR sensor and the microwave sensor, the motion sensing device will operate in an interdependent mode with both the PIR sensor and the microwave sensor operational. The device may automatically change modes if sensing via the current mode is not suitable.

Next, the motion sensing device may zoom in on the area of motion 516. In some embodiments, an adjustable lens will move toward or away from a sensor on a rail or track to provide the zoom capability.

If multiple subjects are detected 518, the subjects may be distinguished from one another based on height 520. In some embodiments, an image detected with a Fresnel lens may be vertically enhanced to permit the device to distinguish between multiple subjects of different sizes. A primary subject may be distinguished from a non-primary subject based on height.

When the primary subject has been identified, the subject may be tracked by the motion sensing device 522. Tracking the subject may be performed by a controller, and may include aiming one or both sensors or changing a zoom level for one or both sensors.

If the primary subject leaves the field of view and is no longer detected 504, the sensors may begin scanning the room for movement 502 once again.

Figure 6:
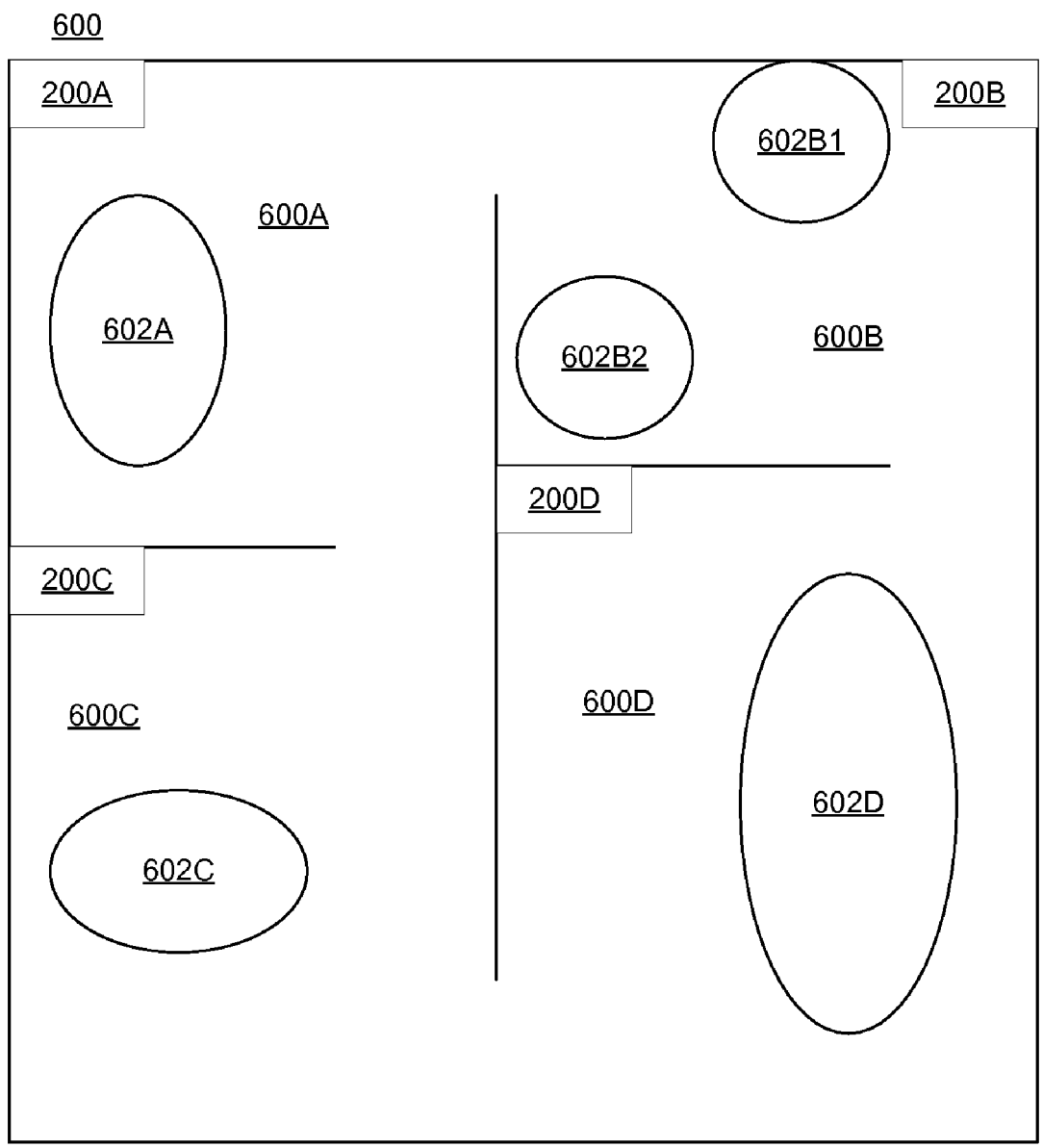
FIG. 6 is a diagram of an in-home motion detection system to monitor patient presence and level of activity according to some embodiments.

FIG. 6 is a diagram of an in-home motion detection system to monitor subject presence and level of activity according to some embodiments. A subject's dwelling 600 may include a plurality of rooms, 600A-D. Each room may include one or more motion sensing device(s) 200A-D, such as that described above with respect to FIGS. 1-5. A single master controller, such as that described above with respect to FIG. 1, may control all of the motion sensing devices 200A-D. The master controller may be located in one of the sensing device units 200A-D, or may be separate from the sensing device units, for example in a desktop or mobile computer or other computing module. The master controller may be coupled to each sensing device unit via a wired or wireless network.

The master controller may be able to infer where a subject will be at a given time based on past sensed patterns of the subject's movements. For example, if the master controller senses a pattern showing that each day the subject is in a living room, 600C, for at least two hours in the afternoon, and the subject is subsequently absent from the living room 600C in the afternoon and instead is spending more time in the bedroom 600A, a caregiver may be notified of this change in the subject's daily activity pattern.

The sensible motion sensing system including a master controller and sensor devices 200A-D may develop a matrix for the home 600. The matrix may be used by the master controller to record sensor detections and to calculate an average a number of sensor detections in each room 600A-D. In some embodiments, this data may be stored in a database accessible by the master controller and/or by a caregiver. The number of detections will allow the master controller to determine a level of activity for the subject. The number of detections will also have an associated standard deviation. For example, if a subject is detected moving among various rooms more frequently in one day than another, and the motion detected is well above or below the average and standard deviation for the subject's movement, a caregiver may be notified.

The use of a matrix and user detection database may also permit the master controller to learn or infer where the subject is frequently located. For each room, it is likely there will be a primary and/or a secondary region where the subject is most frequently located when in the room, 602A, 602B1, 602B2, 602C, 602D. The master controller may use this information to direct each sensor to zoom in on the desired areas without requiring a scan. For example, in a bedroom 600A, the subject may primarily be found in a region on or near a bed 602A, thus, the sensors in sensing device 200A may remain zoomed in on region 602A. In a bathroom, the subject may be primarily found near a bathtub or shower 602B1 or a sink 602B2, thus, the sensors in sensing device 200B may alternate between zooming in on regions 602B1 and 602B2. This may prevent the remote sensing units 200A-D, which may be battery operated, from performing scan cycles or zooms that are unnecessary, thus saving power. It may also reduce the time required to detect a subject when a presence is detected.

Thus, a wireless motion detector including a microwave sensor and a PIR sensor with zoom capability is disclosed in various embodiments. In the above description, numerous specific details are set forth. However, it is understood that embodiments may be practiced without these specific details. In other instances, well-known circuits, structures, and techniques have not been shown in detail in order not to obscure the understanding of this description. Embodiments have been described with reference to specific exemplary embodiments thereof. It will, however, be evident to persons having the benefit of this disclosure that various modifications and changes may be made to these embodiments without departing from the broader spirit and scope of the embodiments described herein. The specification and drawings are, accordingly, to be regarded in an illustrative rather than a restrictive sense.

We claim:

1. An apparatus comprising:
    a first sensor having a first adjustable lens;
    a second sensor having a second adjustable lens; and
    a controller coupled to the first sensor and the second sensor, wherein the controller is to cause the first sensor and the second sensor to operate independently in a first mode and is to cause the first sensor and the second sensor to operate interdependently in a second mode, wherein, in the second mode, the controller is configured to compare simultaneous inputs received from both the first sensor and the second sensor, wherein the controller is configured to determine, based upon data received from one sensor operating in independent mode or both the first sensor and the second sensor operating in interdependent mode, that if either the first sensor or the second sensor is not suitable for motion detection at a particular time, then that unsuitable sensor is not used for motion detection during that time.

2. The apparatus of claim 1, wherein the first sensor is a microwave sensor, wherein the second sensor is a pyroelectric infrared (PIR) sensor, and wherein the first adjustable lens and the second adjustable lens are Fresnel lenses.

3. The apparatus of claim 2, wherein the controller is to cause at least one of the first adjustable lens and the second adjustable lens to zoom in on a subject.

4. The apparatus of claim 3, wherein the first adjustable lens and the second adjustable lens are connected to each other at a hinged joint, and wherein the hinged joint is configured to move along a track to zoom in on the subject.

5. The apparatus of claim 4, wherein the controller is to control the movement of the first adjustable lens and the second adjustable lens along the track.

6. The apparatus of claim 2, wherein the controller is capable of using the first sensor and the second sensor to identify and track a subject based on the height of the subject.

7. The apparatus of claim 2, wherein the first sensor and the second sensor are housed in a single housing and are separated from one another by approximately 3.5 centimeters.

8. The apparatus of claim 1, wherein the controller is configured to determine whether the first sensor is not suitable for motion detection based on a speed of motion of an objected detected by the first sensor, second sensor, or both, based on a distance of the first sensor to the detected object, or based on any combination thereof, and wherein the controller is configured to determine whether the second sensor is not suitable for motion detection based on a speed of motion of an objected detected by the first sensor, second sensor, or both, based on a distance of the second sensor to the detected object, or based on any combination thereof.

9. A method comprising:
monitoring a room with at least two sensors having separate lenses;
determining, based upon data received from the at least two sensors operating in independent mode or in interdependent mode, that if a sensor of the at least two sensors is not suitable for motion detection at particular time, then that unsuitable sensor is not used for motion detection during that time; and
after detecting a subject in the room, changing a zoom level of at least one lens to zoom in on the subject.

10. The method of claim 9, further comprising determining whether the subject is one of a primary subject and a non-primary subject using a height of the primary subject and a height of the non-primary subject as detected by at least one of the two sensors.

11. The method of claim 10, further comprising vertically enhancing the height of the subject to make a height distinction between the primary subject and the non-primary subject.

12. The method of claim 9, wherein monitoring a room with at least two sensors having separate lenses comprises monitoring the room with a PIR sensor for a time period while a microwave sensor is in a power saving mode and switching to monitor the room with the microwave sensor for the time period while the PIR sensor is in a power saving mode.

13. The method of claim 12, wherein the time period is approximately one minute.

14. The method of claim 9, wherein detecting the subject in the room comprises receiving data from the at least two sensors simultaneously and localizing motion sensed by comparing simultaneous inputs from the at least two sensors.

15. The method of claim 9, wherein the determining whether the first sensor is not suitable for motion detection is based on a speed of motion of an objected detected by the first sensor, second sensor, or both, based on a distance of the first sensor to the detected object, or based on any combination thereof, and wherein determining whether the second sensor is not suitable for motion detection is based on a speed of motion of an objected detected by the first sensor, second sensor, or both, based on a distance of the second sensor to the detected object, or based on any combination thereof.

16. A system comprising:
a microwave sensor coupled to a microwave lens and a microwave sensor controller;
a PIR sensor coupled to a PIR lens and a PIR sensor controller; and
a master controller coupled to the PIR sensor controller and the microwave sensor controller, wherein the master controller is configured to perform data processing on data received from at least one of the microwave sensor and the PIR sensor and is configured to direct at least one of the PIR sensor controller and the microwave sensor controller to adjust a zoom level for at least one of the PIR lens and the microwave lens based on the data received from the at least one of the microwave sensor and the PIR sensor and
wherein the master controller is also configured to receive data from the microwave sensor and the PIR sensor simultaneously and to compare simultaneous inputs from the microwave sensor and the PIR sensor.

17. The system of claim 16, wherein the microwave sensor and the PIR sensor are in a single enclosure.

18. The system of claim 17, wherein the master controller is to distinguish between a primary subject and a non-primary subject using a height of the primary subject and a height of the non-primary subject as detected by at least one of the microwave sensor and the PIR sensor.

19. The system of claim 18, wherein the master controller is further to perform vertical enhancement using the height of the primary subject and the height of the non-primary subject as detected by the at least one of the microwave sensor and the PIR sensor.

20. The system of claim 16, wherein the microwave lens and the PIR lens are connected to each other at a hinged joint, and wherein the hinged joint is configured to move along a track to adjust the zoom level.

21. The system of claim 20, wherein the microwave sensor and the PIR sensor are separated by a first distance, and wherein the microwave sensor and the PIR sensor are configured to move along the track to adjust the zoom level.

22. The system of claim 16, wherein the master controller is configured to determine whether to direct the PIR sensor controller to adjust a level of zoom based on a speed of motion of an objected detected by the PIR sensor, microwave sensor, or both, based on a distance of the PIR sensor to the detected object, or based on any combination thereof, and wherein the master controller is configured to determine whether to direct the microwave sensor controller to adjust a level of zoom based on a speed of motion of an objected detected by the PIR sensor, microwave sensor, or both, based on a distance of the microwave sensor to the detected object, or based on any combination thereof.

23. An apparatus comprising:
a first sensor having a first adjustable lens;
a second sensor having a second adjustable lens; and
a controller coupled to the first sensor and the second sensor, wherein the controller is configured to cause the first sensor and the second sensor to operate independently in a first mode and is configured to cause the first motion sensor and the second motion sensor to operate interdependently in a second mode, wherein the first sensor is a microwave sensor and the second sensor is a pyroelectric infrared (PIR) sensor, the first adjustable lens and the second adjustable lens are Fresnel lenses, the controller is configured to cause at least one of the first adjustable lens and the second adjustable lens to zoom in on a subject, and the first adjustable lens and the second adjustable lens are connected to each other at a hinged joint, and wherein the hinged joint is configured to move along a track to zoom in on the subject.

24. A system comprising:
a microwave sensor coupled to a microwave lens and a microwave sensor controller;
a PIR sensor coupled to a PIR lens and a PIR sensor controller; and
a master controller coupled to the PIR sensor controller and the microwave sensor controller, wherein the master controller is to perform data processing on data received from at least one of the microwave sensor and the PIR sensor and is to direct at least one of the PIR sensor controller and the microwave sensor controller to adjust a zoom level for at least one of the PIR lens and the microwave lens based on the data received from the at least one of the microwave sensor and the PIR sensor,
wherein the microwave lens and the PIR lens are connected to each other at a hinged joint, and wherein the hinged joint is configured to move along a track to adjust the zoom level.

\* \* \* \* \*